US010201322B2

(12) United States Patent
Xing

(10) Patent No.: US 10,201,322 B2
(45) Date of Patent: Feb. 12, 2019

(54) COMPUTED TOMOGRAPHY SCANNING APPARATUS, GANTRY ROTATION CONTROL DEVICE AND METHOD THEREOF

(71) Applicant: GE MEDICAL SYSTEMS GLOBAL TECHNOLOGY COMPANY, LLC, Waukesha, WI (US)

(72) Inventor: Zhanfeng Xing, BeiJing (CN)

(73) Assignee: GE MEDICAL SYSTEMS GLOBAL TECHNOLOGY COMPANY, LLC, Waukesha, WI (US)

( * ) Notice: Subject to any disclaimer, the term of this patent is extended or adjusted under 35 U.S.C. 154(b) by 0 days.

(21) Appl. No.: 14/487,684

(22) Filed: Sep. 16, 2014

(65) Prior Publication Data

US 2015/0092910 A1  Apr. 2, 2015

(30) Foreign Application Priority Data

Sep. 30, 2013 (CN) .......................... 2013 1 0461166

(51) Int. Cl.
*A61B 6/03* (2006.01)
*H05G 1/38* (2006.01)
(Continued)

(52) U.S. Cl.
CPC .............. *A61B 6/542* (2013.01); *A61B 6/032* (2013.01); *A61B 6/54* (2013.01); *A61B 6/545* (2013.01);
(Continued)

(58) Field of Classification Search
CPC . H05G 1/38; H05G 1/46; A61B 6/032; A61B 6/54; A61B 6/542; A61B 6/545
(Continued)

(56) References Cited

U.S. PATENT DOCUMENTS 5,175,754 A * 12/1992 Casey .................... A61B 6/035
378/101
5,228,070 A * 7/1993 Mattson ................. A61B 6/032
378/108
(Continued)

FOREIGN PATENT DOCUMENTS

CN       1496713 A       5/2004

OTHER PUBLICATIONS

Machine Translation and Chines Office Action issued in connection with corresponding CN Application No. 201310461166.9 dated Jul. 10, 2018.

*Primary Examiner* — Allen C. Ho
(74) *Attorney, Agent, or Firm* — GE Global Patent Operation; Marc A. Vivenzio

(57) ABSTRACT

A gantry rotation control device for a computed tomography scanning apparatus. The gantry rotation control device includes a radiation dose determination unit for determining radiation doses of the X-rays that will be emitted to each site of the target object to be scanned, a minimum velocity determination unit for determining a minimum rotation velocity of the gantry according to a maximum radiation dose in the determined radiation doses, a maximum velocity determination unit for determining a maximum rotation velocity of the gantry according to the determined minimum rotation velocity, a rotation velocity determination unit for determining a rotation velocity of the gantry at any time during scanning of the target object according to the determined minimum rotation velocity and maximum rotation velocity, and a gantry rotation control unit for controlling the gantry to scan the target object while rotating according to the determined rotation velocity when the target object is to be scanned.

15 Claims, 4 Drawing Sheets

(51) Int. Cl.
*H05G 1/46* (2006.01)
*A61B 6/00* (2006.01)
*G01N 23/046* (2018.01)
*G01P 3/64* (2006.01)
*G01P 3/44* (2006.01)

(52) U.S. Cl.
CPC .............. *G01N 23/046* (2013.01); *G01P 3/44* (2013.01); *G01P 3/64* (2013.01); *H05G 1/38* (2013.01); *H05G 1/46* (2013.01)

(58) Field of Classification Search
USPC .............. 378/4, 15, 16, 91, 96, 97, 108, 109
See application file for complete search history.

(56) References Cited

U.S. PATENT DOCUMENTS

| | | | | |
|---|---|---|---|---|
| 5,661,774 A * | 8/1997 | Gordon | G01N 23/046 | 378/101 |
| 6,212,251 B1 * | 4/2001 | Tomura | A61B 6/032 | 378/15 |
| 6,233,308 B1 * | 5/2001 | Hsieh | A61B 6/032 | 378/19 |
| 6,233,478 B1 * | 5/2001 | Liu | A61B 6/541 | 378/8 |
| 6,269,140 B1 * | 7/2001 | Takagi | A61B 6/541 | 378/8 |
| 6,298,111 B1 * | 10/2001 | Ozaki | A61B 6/541 | 378/114 |
| 6,353,653 B1 * | 3/2002 | Edic | A61B 6/032 | 378/4 |
| 6,370,217 B1 * | 4/2002 | Hu | A61B 6/541 | 378/8 |
| 6,504,894 B2 * | 1/2003 | Pan | A61B 6/032 | 378/15 |
| 6,553,091 B2 * | 4/2003 | Takanashi | A61B 6/035 | 378/15 |
| 6,580,777 B1 * | 6/2003 | Ueki | A61B 6/032 | 378/15 |
| 6,628,742 B2 * | 9/2003 | Pan | A61B 6/032 | 378/4 |
| 6,628,981 B2 * | 9/2003 | Baker | A61B 6/541 | 378/8 |
| 6,639,965 B1 * | 10/2003 | Hsieh | A61B 6/032 | 378/15 |
| 6,816,567 B2 * | 11/2004 | Drummond | A61B 6/032 | 378/16 |
| 6,879,656 B2 * | 4/2005 | Cesmeli | A61B 6/032 | 378/19 |
| 6,901,129 B2 * | 5/2005 | Tachizaki | A61B 6/032 | 378/4 |
| 6,954,513 B2 * | 10/2005 | Horiuchi | A61B 6/583 | 378/165 |
| 7,054,406 B2 * | 5/2006 | Ikeda | A61B 6/032 | 378/4 |
| 7,072,437 B2 * | 7/2006 | Seto | A61B 6/032 | 378/162 |
| 7,076,019 B2 * | 7/2006 | Hagiwara | A61B 6/032 | 378/16 |
| 7,145,982 B2 * | 12/2006 | Ikeda | A61B 6/032 | 378/16 |
| 7,177,386 B2 * | 2/2007 | Mostafavi | A61B 5/1135 | 378/4 |
| 7,221,729 B2 * | 5/2007 | Wakai | A61B 6/032 | 378/108 |
| 7,313,213 B1 * | 12/2007 | Hsieh | A61B 5/0464 | 378/19 |
| 7,376,214 B2 * | 5/2008 | Klingenbeck-Regn | A61B 6/4441 | 378/8 |
| 7,813,473 B2 * | 10/2010 | Edic | A61B 6/032 | 378/197 |
| 7,817,773 B2 * | 10/2010 | Stanton | A61B 6/466 | 378/15 |
| 7,826,587 B1 * | 11/2010 | Langan | A61B 6/032 | 378/16 |
| 8,681,933 B2 * | 3/2014 | Suzuki | A61B 6/0457 | 378/146 |
| 8,842,804 B2 * | 9/2014 | Ooshima | A61B 6/027 | 378/15 |
| 8,848,860 B2 * | 9/2014 | Yazaki | A61B 6/488 | 378/16 |
| 8,873,710 B2 * | 10/2014 | Ling | A61N 5/1047 | 378/65 |
| 9,025,723 B2 * | 5/2015 | Gotman | A61B 6/032 | 378/15 |
| 9,047,702 B2 * | 6/2015 | Schmitt | A61B 6/032 | |
| 9,119,560 B2 * | 9/2015 | Kohara | A61B 6/032 | |
| 9,216,302 B2 * | 12/2015 | Kuwahara | A61N 5/1039 | |
| 9,326,746 B2 * | 5/2016 | Kobayashi | A61B 6/032 | |
| 9,538,976 B2 * | 1/2017 | Keall | A61B 6/4085 | |
| 9,599,578 B2 * | 3/2017 | Yanagita | F16C 17/107 | |
| 9,924,916 B2 * | 3/2018 | Kato | A61B 6/4241 | |
| 2008/0165916 A1 | 7/2008 | Stanton et al. | | |

\* cited by examiner

COMPUTED TOMOGRAPHY SCANNING APPARATUS, GANTRY ROTATION CONTROL DEVICE AND METHOD THEREOF

TECHNICAL FIELD

Embodiments of the present invention relate to the field of Computed Tomography (CT) scanning, and more specifically, to a computed tomography scanning apparatus and a gantry rotation control device and method thereof.

BACKGROUND OF THE INVENTION

A Computed Tomography (CT) scanning apparatus usually comprises a gantry and an x-ray generator capable of emitting X-rays to a target object (e.g. a user to be scanned) for scanning while rotating. The gantry comprises the X-ray generator fixed thereon. Hence, the X-ray generator will rotate as the gantry rotates, and emit X-rays to the target object at the same time, so as to scan each site of the target object to be scanned. The gantry further comprises an imaging device for receiving X-rays (including the X-rays penetrating through the target object) emitted from the X-ray generator. The imaging device converts the received X-rays into electric signals, and sends such electric signals to a console of the CT apparatus. The console of the CT apparatus comprises receiving and processing the electric signals sent by the imaging device so as to obtain a scanning image of the target object including an image of each site of the target object to be scanned. In addition, the console further comprises a display for displaying the scanning image.

The CT apparatus further comprises a gantry rotation control device for controlling movement of the gantry. The existing gantry rotation control device controls the gantry to rotate at a uniform speed. However, when the rating X-ray emitting capacity (generally represented by mA values) of the X-ray generator of the CT apparatus is relatively small and/or the sizes of some sites of the target object to be scanned are relatively big, a scanning imaging with an expected image signal to noise ratio may not be obtained; or, when the rating X-ray emitting capacity of the X-ray generator of the CT apparatus is relatively big and/or the sizes of some sites of the target object to be scanned are relatively small, X-rays with excessive radiation doses may be radiated to these relatively small-sized sites of the target object to be scanned.

Hence, here is expected a CT apparatus for controlling rotation of a gantry at a varied velocity.

BRIEF SUMMARY OF THE INVENTION

One illustrative example of the present invention provides a gantry rotation control device for a computed tomography scanning apparatus. The computed tomography scanning apparatus may comprise an x-ray generator capable of emitting X-rays to a target object for scanning while rotating. The gantry rotation control device may comprise a radiation dose determination unit for determining radiation doses of the X-rays that will be emitted to each site of the target object to be scanned, a minimum velocity determination unit for determining a minimum rotation velocity of the gantry according to a maximum radiation dose in the determined radiation doses, a maximum velocity determination unit for determining a maximum rotation velocity of the gantry according to the determined minimum rotation velocity, a rotation velocity determination unit for determining a rotation velocity of the gantry at any time during scanning of the target object according to the determined minimum rotation velocity and maximum rotation velocity, and a gantry rotation control unit for controlling the gantry to scan the target object while rotating according to the determined rotation velocity when the target object is to be scanned.

Another illustrative example of the present invention provides a gantry movement control method for a computed tomography scanning apparatus. The computed tomography scanning apparatus may comprise an x-ray generator capable of emitting X-rays to a target object for scanning while rotating. The method may comprises: determining radiation doses of the X-rays that will be emitted to each site of the target object to be scanned; determining a minimum rotation velocity of the gantry according to a maximum radiation dose in the determined radiation doses; determining a maximum rotation velocity of the gantry according to the determined minimum rotation velocity; determining a rotation velocity of the gantry at any time during scanning of the target object according to the determined minimum rotation velocity and maximum rotation velocity controlling the gantry to scan the target object while rotating according to the determined rotation velocity, when the target object is to be scanned.

One illustrative example of the present invention provides a computed tomography scanning apparatus, characterized in that, the computed tomography scanning apparatus comprises a gantry rotation control device including a radiation dose determination unit for determining radiation doses of the X-rays that will be emitted to each site of the target object to be scanned, a minimum velocity determination unit for determining a minimum rotation velocity of the gantry according to a maximum radiation dose in the determined radiation doses, a maximum velocity determination unit for determining a maximum rotation velocity of the gantry according to the determined minimum rotation velocity, a rotation velocity determination unit for determining a rotation velocity of the gantry at any time during scanning of the target object according to the determined minimum rotation velocity and maximum rotation velocity, and a gantry rotation control unit for controlling the gantry to scan the target object while rotating according to the determined rotation velocity when the target object is to be scanned.

Other features and aspects will become much clearer through the following detailed depictions, drawings and claims.

BRIEF DESCRIPTION OF THE DRAWINGS

The present invention can be better understood by depicting the illustrative examples of the present invention in combination with the following drawings.

DETAILED DESCRIPTION OF THE INVENTION

The specific embodiments of the present invention will be depicted below; it should be understood that, in order to make a concise depiction of these embodiments, it is impossible for the present description to make detailed depiction to all features of the actual embodiments. It should be understood that, during the actual implementing process of any one embodiment, e.g., during the process of any one engineering project or designing project, in order to realize specific objectives of developers, and to meet system related or commerce related limits, usually various specific decisions will be made, such that a transition from one embodiment to another embodiment will also occur. In addition, it should also be understood that, although efforts made during the developing process may be complicated and lengthy, for ordinary persons skilled in the art who are related with the contents disclosed by the present invention, some changes in design, manufacture or production on the basis of the technical contents disclosed by embodiments of the present invention are only customary technical means, and should not be construed as the contents of the present invention being insufficiently disclosed.

Unless defined otherwise, the technical terms or scientific terms that are used in the claims and the description should have general meanings as understood by persons with ordinary skills in the technical field to which the present invention belongs. Such words as "first" and "second" used in the description and claims of the present invention patent application do not denote any sequence, quantity or significance, and are only used to distinguish different constituting parts. Such words as "one", "a", or "an" only indicate that at least one exists, without denoting quantity limitation. Such words as "including" or "comprising" mean that the elements or objects appearing before the words "including" or "comprising" cover the elements or objects and equivalent elements listed after the words "including" or "comprising", not excluding other elements or objects. Such words as "connection" or "link" are not limited to physical or mechanical connection, and are not limited to direct or indirect connections, either.

Figure 1:
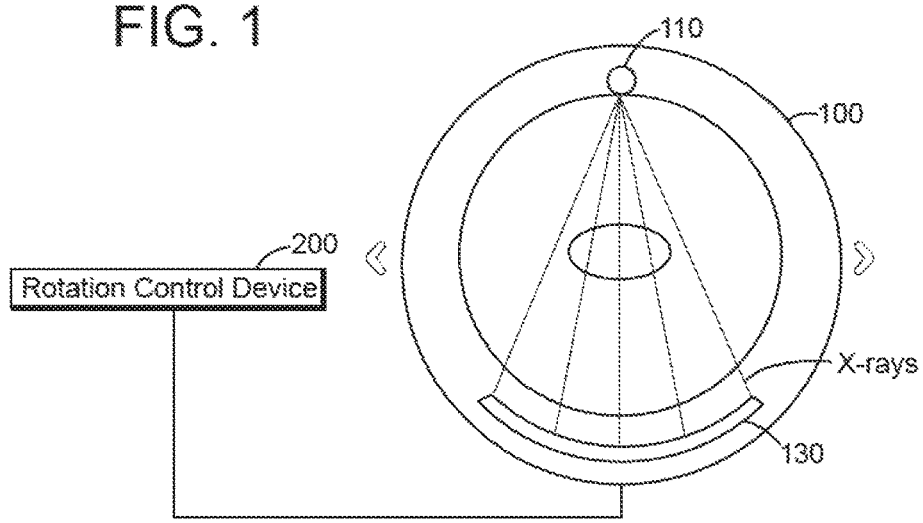
FIG. 1 provides a schematic diagram of a Computed Tomography (CT) scanning system according to an illustrative example.

FIG. 1 provides a schematic diagram of a Computed Tomography (CT) scanning apparatus according to an illustrative example. As shown in FIG. 1, the CT apparatus according to the illustrative example may comprise a gantry 100 compromising an x-ray generator 110 and an imaging device 130, and a gantry rotation control device 200 for controlling rotation of the gantry 100.

The gantry 100 can rotate, and the x-ray generator 110 can emit X-rays to a target object at the same time, thereby scanning the target object (e.g., each site of the target object to be scanned). Hence, the gantry 100 may comprise an X-ray generator 110 that is mounted and fixed on the gantry 100. The X-ray generator 110 can produce X-rays, and can emit X-rays to a target object (e.g., a user to be scanned). The gantry 100 can further comprise an imaging device 130. The imaging device 130 can receive X-rays (including the X-rays penetrating through the target object) emitted from the X-ray generator 110, and can convert the received X-rays into electric signals (i.e., image signals).

Though not shown in the figure, the CT apparatus according to the illustrative example may further comprise an image processor and a display. The imaging device 130 can send the image signals to the image processor, and the image processor can process the received image signals, so as to generate a scanning image including an image of each site of the target object to be scanned. In addition, the image processor can send the generated scanning image to the display, so as to present the scanning image of the target object via the display.

The gantry rotation control device 200 can be connected to the gantry 100, so as to control rotation of the gantry 100 and execute a scanning operation. For example, the gantry rotation control device 200 can send a control signal to, e.g., a driver of an electric motor (not shown), for driving rotation of the gantry 100, so as to control the gantry 100 to rotate at a diverse rotation velocity by controlling operation of the driver, which will be depicted below in details.

According to the illustrative example, the gantry rotation control device 200 can determine the rotation velocity of the gantry 100 during the scanning of the target object in accordance with hardware specifications of various assemblies comprised in the CT apparatus, size or magnitude of the target object and/or the expected image signal to noise ratio of the scanning image that will be obtained by scanning the target object, and can control rotation of the gantry 100 in accordance with the determined rotation velocity. Here, hardware specifications of the CT apparatus may include the rating X-ray emitting capacity (generally represented by mA (milliampere) values) of the X-ray generator 110, and the rating maximum rotation velocity and the rating maximum acceleration of the gantry 100.

Figure 2:
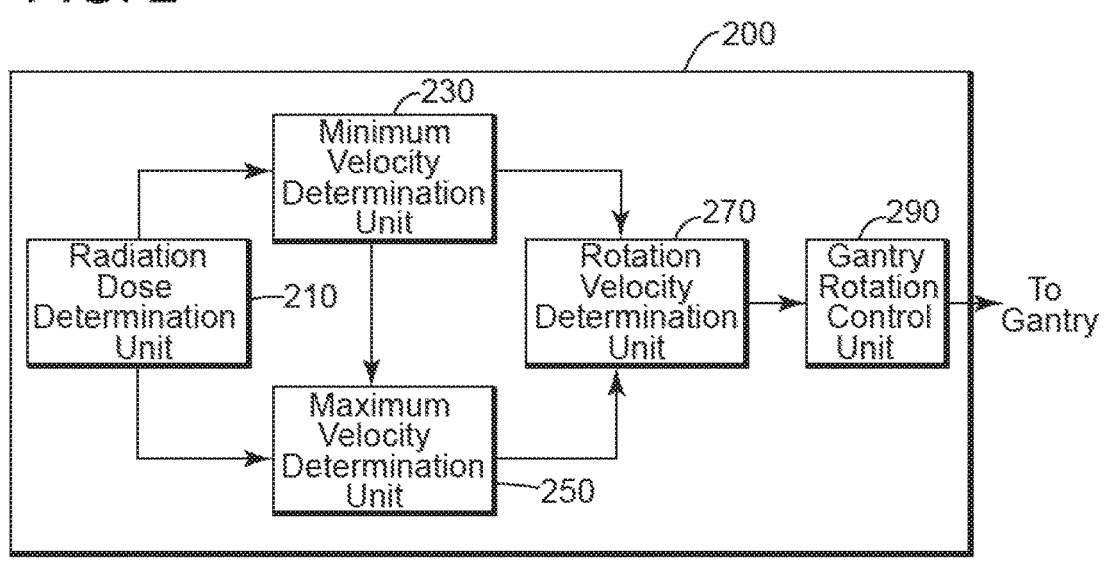
FIG. 2 provides a schematic block diagram of a gantry rotation control device according to an illustrative example.

FIG. 2 provides a schematic block diagram of a rotation control device 200 according to an illustrative example. The rotation control device 200 according to the illustrative example may comprise a radiation dose determination unit 210, a minimum velocity determination unit 230, a maximum velocity determination unit 250, a rotation velocity determination unit 270 and a gantry rotation control unit 290.

The radiation dose determination unit 210 can determine radiation doses of the X-rays that will be emitted to each site of the target object to be scanned when the gantry 100 (i.e., including the X-ray generator 110 in the gantry 100) scans each site to be scanned. For example, the radiation dose determination unit 210 can firstly make the gantry 100 conduct a scout scan of the target object, thereby obtaining a scout image. Then, the radiation dose determination unit 210 determines radiation doses of the X-rays that will be emitted by the x-ray generator 110 to each site of the target object to be scanned, according to the obtained scout image and an expected image signal to noise ratio. The radiation dose can be represented by mAs (milliampere second), i.e., the rating X-ray emitting capacity (mA) of the X-ray generator 110 is multiplied by the scanning time (s) in which the X-ray generator 110 scans the site to be scanned.

Figure 5:
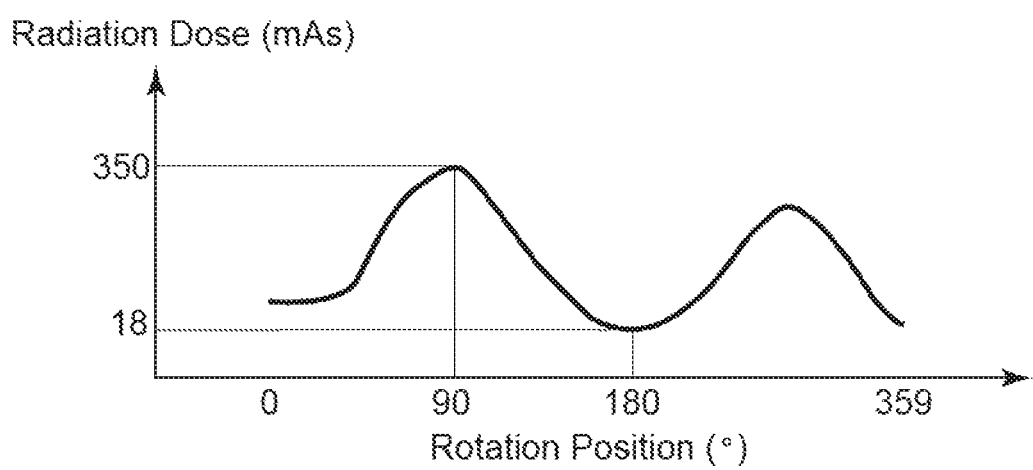
FIG. 5 provides a curve diagram for relation between rotation positions of the gantry and radiation doses according to an illustrative example.

FIG. 5 provides a curve diagram for relation between rotation positions of the gantry 100 and radiation doses according to an illustrative example.

In the current illustrative example, when scanning operation is executed, the gantry 100 can rotate 360°, thereby scanning each site of the target object to be scanned. Because magnitude or size of the sites of the target object to be scanned is different, and/or because the ability of the sites of the target object to be scanned for absorbing X-rays is different, in order to obtain a scanning image with an expected image signal to noise ratio, radiation doses of X-rays which are emitted to the target object when the gantry 100 rotates to different positions can be different. As shown in FIG. 5, when scanning operation is started, the gantry 100 can start rotating from the initial position (i.e., 0°), and emit X-rays to the target object. When the gantry 100 rotates to a position near 90°, the radiation dose reaches the maximum value, and when the gantry 100 rotates to a position near 180°, the radiation dose reaches the minimum value. When rotating one circumference and returning to the initial position (i.e., 0°), the x-ray generator 110 can stop emitting X-rays to the target object, and finish scanning operation.

In the current illustrative example, the functions and operations of the radiation dose determination unit 210 as described herein can be realized through the mA modulation techniques known to persons skilled in the art, such that a curve for relation between rotation positions and radiation doses as shown in FIG. 5 can be obtained.

When radiation doses of the X-rays that will be emitted by the x-ray generator 110 to each site of the target object to be scanned are determined, the radiation dose determination unit 210 can send information related to the determined radiation doses to the minimum velocity determination unit 230. Here, information related to the determined radiation doses can comprise information related to the curve, as shown in FIG. 5. However, the illustrative example is not exhaustive, and in other illustrative examples, information related to the determined radiation doses can be a lookup table, which records the relation between rotation positions and radiation doses.

When information related to the determined radiation doses is received, the minimum velocity determination unit 230 can determine the minimum rotation velocity of the gantry 100 according to the maximum radiation dose in the determined radiation doses. During the scanning, the lower the rotation velocity of the gantry 100 is, the greater the radiation dose of X-rays from the x-ray generator 110 to the target object is. Hence, at the rotation position corresponding to the maximum radiation dose, the rotation velocity of the gantry 100 can be minimal.

However, the illustrative example is not exhaustive, and in other illustrative examples, the radiation dose determination unit 210 can send information related to the maximum radiation dose in the determined radiation doses to the minimum velocity determination unit 230.

For example, the minimum velocity determination unit 230 can compute the minimum rotation velocity $V_{min}$ according to the following formula 1:

$$V_{min} = mA_{max}/mAs_{max} \qquad (1).$$

In the formula 1, $mA_{max}$ is the rating maximum X-ray emitting capacity of the x-ray generator 110 (i.e., the X-ray generator 110 in the gantry 100), and $mAs_{max}$ is the maximum radiation dose (e.g., the peak value to which the rotation position near 90° corresponds in FIG. 5) in the determined radiation doses. In the current illustrative example, the unit for the rotation velocity of the gantry 100 can be RPS (rotations per second).

When the minimum rotation velocity $V_{min}$ of the gantry 100 is determined, the minimum velocity determination unit 230 can send information related to the determined minimum rotation velocity $V_{min}$ to the maximum velocity determination unit 250 and the rotation velocity determination unit 270. When information related to the determined minimum rotation velocity is received, the maximum velocity determination unit 250 can determine the maximum rotation velocity of the gantry 100 according to the determined minimum rotation velocity $V_{min}$.

For example, the maximum velocity determination unit 250 can compute the first maximum rotation velocity $V_{max1}$ according to the following formula 2:

$$\begin{cases} S = t \times (V_{min} + V_{max1})/2 \\ V_{max1} = V_{min} + a \times t \end{cases} \qquad (2)$$

In formula 2, S is a distance by which the gantry 100 passes when rotating from a position (e.g., a position near 90° as shown in FIG. 5) corresponding to a site of the target object to be scanned that corresponds to the maximum radiation dose to another position (e.g., a position near 180° as shown in FIG. 5) corresponding to a site of the target object to be scanned that corresponds to the minimum radiation dose in the determined radiation doses. Vmin is the determined minimum rotation velocity of the gantry 100, a is the rating maximum acceleration of the gantry 100, and t is time that is needed when the gantry 100 is accelerated at the rating maximum acceleration a from the minimum rotation velocity Vmin to the maximum rotation velocity Vmax1. The unit for S can be circumference, for example, the distance S by which the gantry 100 passes when rotating from the position near 90° in FIG. 5 to the position near 180° in FIG. 5 can be about ¼ circumference. Here, the radiation dose determination unit 210 can send information related to the determined radiation doses to the maximum velocity determination unit 250, or can send information related to only the minimum radiation dose in the determined radiation doses to the maximum velocity determination unit 250.

However, the illustrative example is not exhaustive, and in other illustrative examples, the maximum velocity determination unit 250 can also determine the first maximum rotation velocity $V_{max1}$ when the rating maximum rotation velocity of the gantry 100 is taken into consideration. That is, when the $V_{max1}$ computed according to the formula 2 is greater than the rating maximum rotation velocity of the gantry 100, the maximum velocity determination unit 250 can determine the rating maximum rotation velocity of the gantry 100 to be the first maximum rotation velocity $V_{max1}$.

The maximum velocity determination unit 250 can also compute the second maximum rotation velocity $V_{max2}$ according to the following formula 3:

$$V_{max2} = mA_{max}/mAs_{min} \qquad (3).$$

In formula 3, $mA_{max}$ is the rating maximum X-ray emitting capacity of the x-ray generator 110, and $mAs_{min}$ is the minimum radiation dose (e.g. the peak value to which the rotation position near 180° corresponds in FIG. 5) in the determined radiation doses.

Then, the maximum velocity determination unit 250 can determine whether the first maximum rotation velocity $V_{max1}$ greater than the second maximum rotation velocity $V_{max2}$. When it is determined that the first maximum rotation velocity $V_{max1}$ is greater than the second maximum rotation velocity $V_{max2}$, the maximum velocity determination unit 250 can determine the second maximum rotation velocity $V_{max2}$ to be the maximum rotation velocity of the gantry 100. When the first maximum rotation velocity $V_{max1}$ is not greater than the second maximum rotation velocity $V_{max2}$, the maximum velocity determination unit 250 can determine the first maximum rotation velocity $V_{max1}$ to be the maximum rotation velocity of the gantry 100.

When the maximum rotation velocity of the gantry 100 is determined, the maximum velocity determination unit 250 can send information related to the determined maximum rotation velocity to the rotation velocity determination unit 270. When information related to the determined minimum rotation velocity $V_{min}$ and information related to the determined maximum rotation velocity are received, the rotation velocity determination unit 270 can determine a rotation velocity of the gantry 100 at any time during the scanning of the target object according to the determined minimum rotation velocity $V_{min}$ and maximum rotation velocity. For example, the rotation velocity determination unit 270 can obtain a curve of the rotation velocity of the gantry 100 relative to time or rotation position.

For example, because the gantry 100 starts rotating from the initial position when starting scanning the target object, and returns to the initial position after scanning is finished, the rotation velocity determination unit 270 can divide the rotating process of the gantry 100 into a decelerating process of rotating from the position (the position near 90° in FIG. 5) corresponding to the maximum rotation velocity $V_{max}$ to the position (the position near 180° in FIG. 5) corresponding to the minimum rotation velocity $V_{min}$ and an accelerating process of rotating from the position (the position near 180° in FIG. 5) corresponding to the minimum rotation velocity to the position (the position near 90° in FIG. 5) corresponding to the maximum rotation velocity.

During the decelerating process, the rotation velocity determination unit 270 can obtain the rotation velocity $V_t$ at time t according to the following formula 4:

$$V_t = V_{max} - a_1 t \quad (4).$$

In formula 4, $v_{max}$ is the maximum rotation velocity of the gantry 100 that is determined by the maximum velocity determination unit 250, and $a_1$ is the acceleration of the gantry 100 when rotating at a decelerating speed, and can be decided by the braking ability of the braking device (not shown) of the gantry 100.

During the accelerating process, the rotation velocity determination unit 270 can obtain the rotation velocity $V_t$ at time t according to the following formula 5:

$$V_t = V_{min} + a_2 t \quad (5).$$

In formula 5, $v_{min}$ is the minimum rotation velocity of the gantry 100 that is determined by the minimum velocity determination unit 230, and $a_2$ is the acceleration of the gantry 100 when rotating at an accelerating speed, and can be decided by the driving ability of the driver (not shown) of the gantry 100.

When the rotation velocity of the gantry 100 at any time during scanning of the target object is determined, the rotation velocity determination unit 270 can send information related to the determined rotation velocity to the gantry rotation control unit 290. Here, information related to the determined rotation velocity can comprise information related to the curve of the rotation velocity of the gantry 100 relative to time or rotation position, or can be a lookup table that records the relation of the rotation velocity of the gantry 100 relative to time or rotation position.

When information related to the determined rotation velocity is received, the gantry rotation control unit 290 can generate gantry control signals according to information related to the determined rotation velocity, and provide the gantry control signals as generated to the gantry 100 (e.g., the driver (not shown) of the gantry). Hence, the gantry 100 will rotate according to the determined rotation velocity when conducting scanning operation.

According to the illustrative example, the rotation control device 200 and the CT apparatus comprising the rotation control device 200 can determine the rotation velocity of the gantry 100 in accordance with hardware specifications of various assemblies comprised in the CT apparatus, size or magnitude of the target object, and/or the expected image signal to noise ratio of the scanning image that will be obtained by scanning the target object. Hence, the gantry 100 can rotate at the determined rotation velocity, e.g. rotate at a varied speed, during the scanning, so a scanning image with an expected signal to noise ratio can be obtained, scanning time is shortened, radiation doses acceptable to the target object are decreased.

Figure 3:
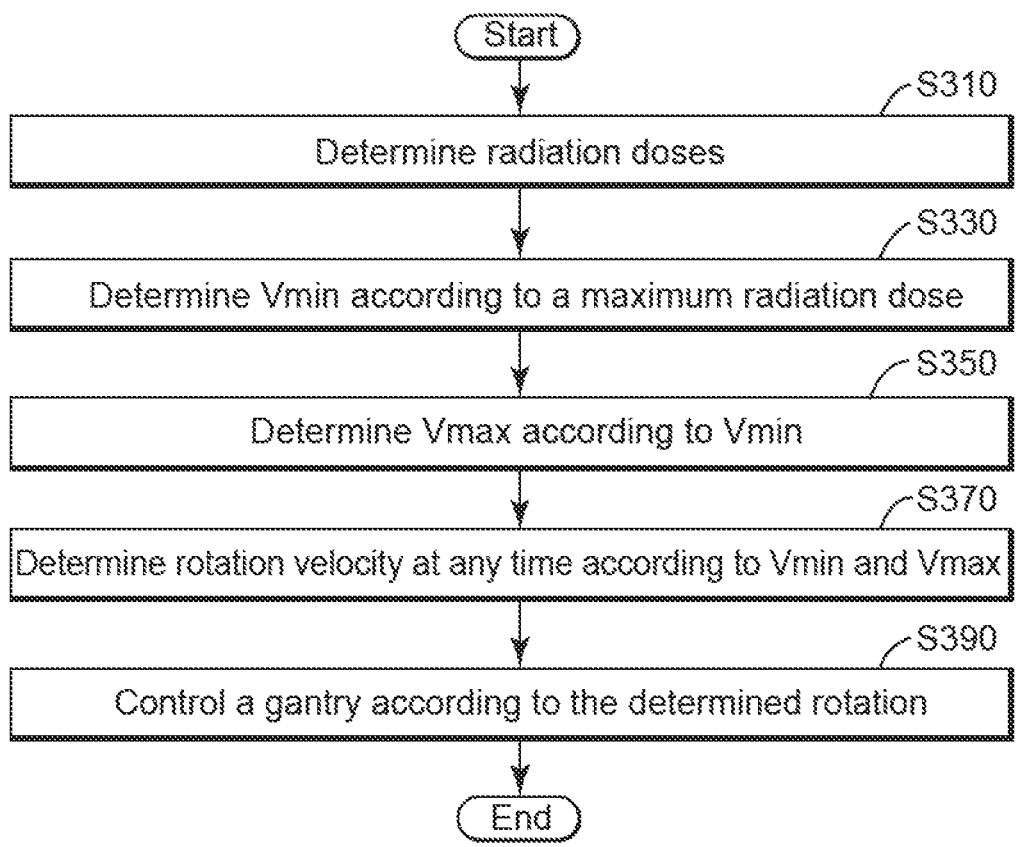
FIG. 3 provides a flow chart for a gantry movement control method according to an illustrative example.

FIG. 3 provides a flow chart for a gantry movement control method according to an illustrative example. The gantry movement control method according to the illustrative example can be used to control the gantry 100 in the Computed Tomography (CT) scanning apparatus as stated above, so as to enable the x-ray generator 110 to emit X-rays to the target object for scanning while rotating. For simplicity, repetitive depiction of the same or similar elements or features will be omitted.

As shown in FIG. 3, radiation doses of the X-rays that will be emitted to each site of the target object to be scanned can be determined (S310). For example, the gantry 100 can be controlled to conduct scout scan of the target object, so as to obtain a scout image, and then radiation doses of the X-rays that will be emitted by the x-ray generator 110 to each site of the target object to be scanned can be determined according to the obtained scout image and an expected image signal to noise ratio.

The minimum rotation velocity $V_{min}$ of the gantry 100 can be determined according to the maximum radiation dose in the determined radiation doses (S330). For example, the minimum rotation velocity $V_{min}$ of the gantry can be computed according to the following formula 1:

$$V_{min} = mA_{max}/mAs_{max} \quad (1).$$

In formula 1, $mA_{max}$ is the rating maximum X-ray emitting capacity of the x-ray generator 110, and $mAs_{max}$ is the maximum radiation dose in the determined radiation doses.

The maximum rotation velocity $V_{max}$ of the gantry 100 can be determined according to the determined minimum rotation velocity $V_{min}$ (S350).

Figure 4:
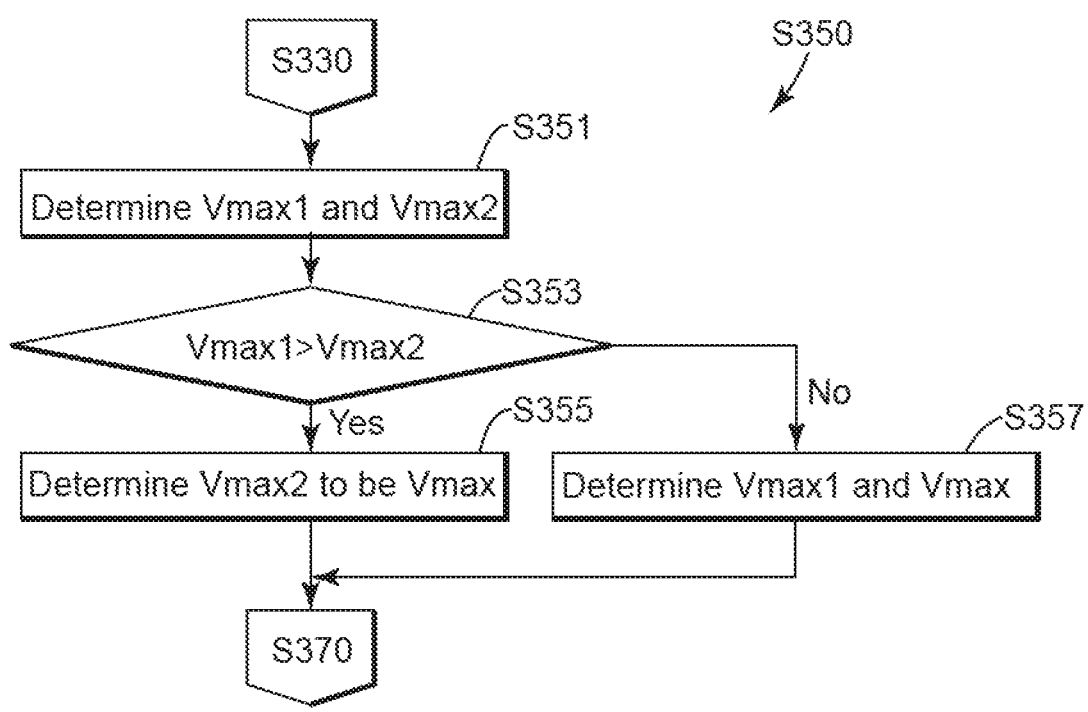
FIG. 4 provides a detailed flow chart for steps of determining a maximum rotation velocity of a gantry according to an illustrative example.

FIG. 4 provides a detailed flow chart for determining a maximum rotation velocity $V_{max}$ of a gantry (S350) according to an illustrative example.

As shown in FIG. 4, the first maximum rotation velocity $V_{max1}$ and the second maximum rotation velocity $V_{max2}$ can be determined (S351).

For example, the first maximum rotation velocity $V_{max1}$ can be computed according to the following formula 2

$$\begin{cases} S = t \times (V_{min} + V_{max1})/2 \\ V_{max1} = V_{min} + a \times t \end{cases} \quad (2)$$

In the formula 2, S is a distance by which the gantry 100 passes when rotating from a position corresponding to a site of the target object to be scanned that corresponds to the maximum radiation dose to another position corresponding to a site of the target object to be scanned that corresponds to the minimum radiation dose in the determined radiation doses. Vmin is the determined minimum rotation velocity of the gantry 100, a is a rating maximum acceleration of the gantry 100, and t is time that is needed when the gantry 100 is accelerated at the rating maximum acceleration a from the minimum rotation velocity Vmin to the first maximum rotation velocity Vmax1.

Here, when the $V_{max1}$ computed according to formula 2 is greater than the rating maximum rotation velocity of the gantry 100, the rating maximum rotation velocity of the gantry 100 can be determined to be the first maximum rotation velocity $V_{max1}$.

In addition, the second maximum rotation velocity $V_{max2}$ can be computed according to the following formula 3

$$V_{max2} = mA_{max}/mAs_{min} \quad (3).$$

In formula 3, $mA_{max}$ is the rating maximum X-ray emitting capacity of the x-ray generator 110, and $mAs_{min}$ is the minimum radiation dose in the determined radiation doses.

Then, it can be determined whether the first maximum rotation velocity $V_{max1}$ is greater than the second maximum rotation velocity $V_{max2}$.

When it is determined that the first maximum rotation velocity $V_{max1}$ is greater than the second maximum rotation velocity $V_{max2}$ (Yes at S353), the second maximum rotation velocity $V_{max2}$ can be determined to be the maximum rotation velocity $V_{max}$ of the gantry 100 (S355). When it is determined that the first maximum rotation velocity $V_{max1}$ is not greater than the second maximum rotation velocity $V_{max}$ (No at S353), the first maximum rotation velocity $V_{max1}$ can be determined to be the maximum rotation velocity $V_{max}$ of the gantry 100 (S357).

Returning to FIG. 3, when the minimum rotation velocity $V_{min}$ and the maximum rotation velocity $V_{max}$ are determined (S3501, the rotation velocity of the gantry 100 at any time and/or any rotation position during scanning of the target object can be determined according to the determined minimum rotation velocity $V_{min}$ and maximum rotation velocity $V_{max}$ (S370). Since the method of determining the rotation velocity of the gantry 100 has been depicted above, no more repetitive depictions are provided here.

After the rotation velocity of the gantry 100 is determined, during scanning of the target object, the gantry 100 can be controlled to rotate according to the determined rotation velocity, and to scan the target object at the same time (S390).

According to the illustrative example, the gantry movement control method can determine the rotation velocity of the gantry 100 in accordance with hardware specifications of various assemblies comprised in the CT apparatus, size or magnitude of the target object, and/or the expected image signal to noise ratio of the scanning image that will be obtained by scanning the target object. Hence, the gantry 100 can rotate at the determined rotation velocity, e.g., rotate at a varied speed, during the scanning, so a scanning image with an expected signal to noise ratio can be obtained, scanning time is shortened, radiation doses acceptable to the target object are decreased.

Some illustrative examples have been depicted above. However, it can be understood that various amendments can be made. For example, if the technology as depicted is executed in a different order, and/or, if the assemblies in the system, framework, device or electric circuit as depicted are combined in a different manner and/or substituted or supplemented by additional assemblies or their equivalents, an appropriate result can be achieved. Accordingly, other embodiments all fall within the protection scopes of the claims.

What is claimed is:

1. A gantry rotation control device for a computed tomography scanning apparatus, the computed tomography scanning apparatus comprising a gantry rotatable around a target object and an x-ray generator coupled to the gantry, the x-ray generator capable of emitting X-rays to the target object for scanning while rotating, the gantry rotation control device connected to the gantry and comprising a computer configured to:

determine radiation doses of the X-rays that will be emitted to each site of the target object to be scanned;

determine a minimum rotation velocity of the gantry according to a maximum radiation dose in the determined radiation doses;

determine a maximum rotation velocity of the gantry according to the determined minimum rotation velocity;

determine a rotation velocity of the gantry at any time during scanning of the target object according to the determined minimum rotation velocity and the determined maximum rotation velocity; and control the gantry to scan the target object while rotating the gantry according to the determined rotation velocity, when the target object is to be scanned.

2. The gantry rotation control device according to claim 1, further configured to:

control the gantry to conduct a scout scan of the target object to obtain a scout image; and determine radiation doses of the X-rays that will be emitted by the x-ray generator to each site of the target object to be scanned, according to the obtained scout image and an expected image signal-to-noise ratio.

3. The gantry rotation control device according to claim 1, further configured to:

compute the minimum rotation velocity $V_{min}$ of the gantry according to:

$$V_{min} = mA_{max}/mAs_{max},$$

wherein $mA_{max}$ is a rating maximum X-ray emitting capacity of the x-ray generator, and $mAs_{max}$ is the maximum radiation dose in the determined radiation doses.

4. The gantry rotation control device according to claim 1, further configured to:

compute a first maximum rotation velocity $V_{max1}$ according to:

$$\begin{cases} S = t \times (V_{min} + V_{max1})/2 \\ V_{max1} = V_{min} + a \times t \end{cases},$$

wherein S is a distance by which the gantry passes when rotating from a position corresponding to a site of the target object to be scanned that corresponds to the maximum radiation dose to another position corresponding to a site of the target object to be scanned that corresponds to the minimum radiation dose in the determined radiation doses, $V_{min}$ is the determined minimum rotation velocity of the gantry, and a is a rating maximum acceleration of the gantry;

compute a second maximum rotation velocity $V_{max2}$ according to:

$$V_{max2} = mA_{max}/mAs_{min},$$

wherein $mA_{max}$ is a rating maximum X-ray emitting capacity of the x-ray generator, and $mAs_{min}$ is the minimum radiation dose in the determined radiation doses;

determine whether the first maximum rotation velocity is greater than the second maximum rotation velocity;

determine the second maximum rotation velocity to be the maximum rotation velocity of the gantry when it is determined that the first maximum rotation velocity is greater than the second maximum rotation velocity, and determine the first maximum rotation velocity to be the maximum rotation velocity of the gantry when it is determined that the first maximum rotation velocity is not greater than the second maximum rotation velocity; and determine the first maximum rotation velocity to be the maximum rotation velocity of the gantry when it is determined that the first maximum rotation velocity is not greater than the second maximum rotation velocity.

5. The gantry rotation control device according to claim 4, further configured to determine the rating maximum rotation velocity of the gantry to be the first maximum rotation velocity when $V_{max1}$ is greater than the rating maximum rotation velocity of the gantry.

6. A method for determining rotation velocity of a gantry having an x-ray generator coupled to the gantry, the x-ray generator capable of emitting X-rays to a target object, said method comprising:

providing a gantry rotation control device comprising a computer;

computing via the computer a minimum rotation velocity $V_{min}$ for a gantry as a ratio of a rating maximum X-ray emitting capacity $mA_{max}$ of the x-ray generator to a maximum radiation dose $mAs_{max}$ corresponding to a first rotation position for the gantry, the maximum radiation dose $mAs_{max}$ found on a curve that relates rotation positions of the gantry to radiation dose;

computing via the computer a first maximum rotation velocity $V_{max1}$ based on a distance S by which the gantry passes when rotating from a position corresponding to the maximum radiation dose $mAs_{max}$ to another position corresponding to a site of the target object to be scanned that with a minimum radiation dose found on the curve;

computing via the computer a second maximum rotation velocity $V_{max2}$ as a ratio of the rating maximum X-ray $mA_{max}$ emitting capacity of the gantry to a maximum rotation dose $mAs_{min}$ corresponding to a second position for the gantry, which is different from the first position, as found on the curve; and comparing via the computer the first maximum rotation velocity $V_{max1}$ to the second maximum rotation velocity $V_{max2}$ to determine a rotation velocity for the gantry.

7. The method according to claim 6, further comprising: controlling the gantry to conduct a scout scan of the target object, so as to obtain a scout image; and determining radiation doses of the X-rays that will be emitted by the x-ray generator to each site of the target object to be scanned, according to the obtained scout image and an expected image signal-to-noise ratio.

8. The method according to claim 6, wherein the minimum rotation velocity $V_{min}$ of the gantry is calculated according to:

$$V_{min} = mA_{max}/mAs_{max},$$

wherein $mA_{max}$ is a rating maximum X-ray emitting capacity of the x-ray generator, and $mAs_{max}$ is the maximum radiation dose in the determined radiation doses.

9. The method according to claim 6, wherein the first maximum rotation velocity Vmax1 is calculated according to:

$$S = \frac{t \times (V_{min} + V_{max1})}{2},$$

$$V_{max1} = V_{min} + \alpha \times t$$

wherein $V_{min}$ is the determined minimum rotation velocity of the gantry, $\alpha$ is a rating maximum acceleration of the gantry, and t is time that is needed when the gantry is accelerated at the rating maximum acceleration $\alpha$ from the minimum rotation velocity $V_{min}$ to the first maximum rotation velocity $V_{max1}$;

the second maximum rotation velocity $V_{max2}$ is calculated according to:

$$V_{max2} = mA_{max}/mAs_{min},$$

wherein the second maximum rotation velocity is the maximum rotation velocity of the gantry when the first maximum rotation velocity is greater than the second maximum rotation velocity, and wherein the first maximum rotation velocity is the maximum rotation velocity of the gantry when the first maximum rotation velocity is not greater than the second maximum rotation velocity.

10. The method according to claim 9, wherein computing the first maximum rotation velocity, the rating maximum rotation velocity of the gantry is determined to be the first maximum rotation velocity when $V_{max1}$ is greater than the rating maximum rotation velocity of the gantry.

11. A computed tomography scanning apparatus, comprising:

a gantry rotatable around a target object;

an x-ray generator coupled to the gantry and capable of emitting X-rays to a target object for scanning while the gantry rotates; and a gantry rotation control device configured to control operation of the gantry and the x-ray generator, wherein the gantry rotation control device comprises a computer configured to:

determine radiation doses of the X-rays that will be emitted to each site of the target object to be scanned;

determine a minimum rotation velocity of the gantry according to a maximum radiation dose in the determined radiation doses;

determine a maximum rotation velocity of the gantry according to the determined minimum rotation velocity;

determine a rotation velocity of the gantry at any time during scanning of the target object according to the determined minimum rotation velocity and maximum rotation velocity; and control the gantry to scan the target object while rotating according to the determined rotation velocity, when the target object is to be scanned.

12. The computed tomography scanning apparatus according to claim 11, wherein the gantry rotation control device is configured to:

control the gantry to conduct a scout scan of the target object to obtain a scout image; and determine radiation doses of the X-rays that will be emitted by the x-ray generator to each site of the target object to be scanned, according to the obtained scout image and an expected image signal to noise ratio.

13. The computed tomography scanning apparatus according to claim 11, wherein the gantry rotation control device is configured:

compute the minimum rotation velocity $V_{min}$ of the gantry according to:

$$V_{min}=mA_{max}/mAs_{max},$$

wherein $mA_{max}$ is a rating maximum X-ray emitting capacity of the x-ray generator, and $mAs_{max}$ is the maximum radiation dose in the determined radiation doses.

14. The computed tomography scanning apparatus according to claim 11, wherein the electronic gantry rotation control device is configured to:

compute a first maximum rotation velocity $V_{max1}$ according to:

$$\begin{cases} S = t \times (V_{min} + V_{max1})/2 \\ V_{max1} = V_{min} + a \times t \end{cases},$$

wherein S is a distance by which the gantry passes when rotating from a position corresponding to a site of the target object to be scanned that corresponds to the maximum radiation dose to another position corresponding to a site of the target object to be scanned that corresponds to the minimum radiation dose in the determined radiation doses, $V_{min}$ is the determined minimum rotation velocity of the gantry, and a is a rating maximum acceleration of the gantry;

compute a second maximum rotation velocity $V_{max2}$ according to:

$$V_{max2}=mA_{max}/mAs_{min},$$

wherein $mA_{max}$ is a rating maximum X-ray emitting capacity of the x-ray generator, and $mAs_{min}$ is the minimum radiation dose in the determined radiation doses;

determine whether the first maximum rotation velocity is greater than the second maximum rotation velocity;

determine the second maximum rotation velocity to be the maximum rotation velocity of the gantry when it is determined that the first maximum rotation velocity is greater than the second maximum rotation velocity; and determine the first maximum rotation velocity to be the maximum rotation velocity of the gantry when it is determined that the first maximum rotation velocity is not greater than the second maximum rotation velocity.

15. The computed tomography scanning apparatus according to claim 14, wherein the gantry control device is configured to determine the rating maximum rotation velocity of the gantry to be the first maximum rotation velocity when $V_{max1}$ is greater than the rating maximum rotation velocity of the gantry.

* * * * *